United States Patent
Seida et al.

(10) Patent No.: US 9,772,312 B2
(45) Date of Patent: Sep. 26, 2017

(54) DEVICE AND METHOD FOR DETECTING DEPOSITS

(71) Applicant: SOLENIS TECHNOLOGIES, L.P., Schaffhausen (CH)

(72) Inventors: Frank Seida, Werne (DE); Christian Flocken, Krefeld (DE); Patric Bierganns, Frefeld (DE); Michael Schultz, Bad Durrenbert (DE)

(73) Assignee: Solenis Technologies, L.P. (CH)

( * ) Notice: Subject to any disclaimer, the term of this patent is extended or adjusted under 35 U.S.C. 154(b) by 198 days.

(21) Appl. No.: 14/367,268

(22) PCT Filed: Dec. 20, 2012

(86) PCT No.: PCT/EP2012/076314
§ 371 (c)(1),
(2) Date: Jun. 20, 2014

(87) PCT Pub. No.: WO2013/092820
PCT Pub. Date: Jun. 27, 2013

(65) Prior Publication Data
US 2015/0000407 A1   Jan. 1, 2015

(30) Foreign Application Priority Data
Dec. 22, 2011   (EP) .................... 11010108

(51) Int. Cl.
*G01N 29/07* (2006.01)
*G01N 29/04* (2006.01)
(Continued)

(52) U.S. Cl.
CPC .......... *G01N 29/043* (2013.01); *G01B 17/02* (2013.01); *G01N 17/008* (2013.01); *G01N 29/00* (2013.01);
(Continued)

(58) Field of Classification Search
CPC ...... G01N 29/043; G01N 29/00; G01N 29/44; G01N 29/07; G01N 29/024; G01N 29/222;
(Continued)

(56) References Cited

U.S. PATENT DOCUMENTS 5,092,176 A   3/1992   Buttram et al.
6,161,435 A * 12/2000   Bond .................... B01D 61/12
                                                          210/785
(Continued)

FOREIGN PATENT DOCUMENTS

EP   1816107   6/2006
WO   2009141135   11/2009

OTHER PUBLICATIONS

International Search Report, PCT/EP2012/076314, pp. 1-2, dated Mar. 18, 2013.

*Primary Examiner* — Laura Martin
*Assistant Examiner* — Rose M Miller
(74) *Attorney, Agent, or Firm* — Michael J Herman; Joanne Rossi

(57) ABSTRACT

The present invention relates to a method and device for detecting and analyzing deposits in liquid-bearing systems. More particularly, the device relates to being able to detect and analyze deposits in a liquid-bearing systems such as industrial plants that use and store fluids. The method relates to being able to determine a distribution of the run time of a detected ultrasonic reflection signal and analyzing the distribution to determine if deposits are deposited onto a heated reflecting area.

14 Claims, 4 Drawing Sheets

(51) Int. Cl.
    *G01N 29/00*     (2006.01)
    *G01N 17/00*     (2006.01)
    *G01B 17/02*     (2006.01)
    *G01N 29/44*     (2006.01)

(52) U.S. Cl.
    CPC ..... *G01N 29/44* (2013.01); *G01N 2291/0231* (2013.01); *G01N 2291/0237* (2013.01); *G01N 2291/0289* (2013.01); *G01N 2291/044* (2013.01); *G01N 2291/045* (2013.01); *G01N 2291/101* (2013.01); *G01N 2291/2636* (2013.01)

(58) Field of Classification Search
    CPC ... G01N 2291/0231; G01N 2291/0289; G01N 2291/044; G01N 2291/045; G01N 2291/101; G01N 2291/2636; G01N 2291/011; G01N 2291/02416; G01N 2291/0251; G01N 2291/02656; G01N 2291/02854; G01N 17/008; G01B 17/02
    USPC .................................. 73/597, 598, 627, 629
    See application file for complete search history.

(56) References Cited

U.S. PATENT DOCUMENTS

| | | | |
|---|---|---|---|
| 6,250,140 B1* | 6/2001 | Kouznetsov | G01N 17/008 436/6 |
| 6,973,842 B1* | 12/2005 | Feller | G01F 1/66 73/597 |
| 2007/0006656 A1 | 1/2007 | Batzinger et al. | |
| 2010/0225477 A1* | 9/2010 | Livchak | F23J 3/026 340/540 |
| 2014/0177673 A1* | 6/2014 | Bliss | G01N 25/18 374/165 |

* cited by examiner

DEVICE AND METHOD FOR DETECTING DEPOSITS

BACKGROUND

The present invention relates to a device and a method for detecting and analyzing deposits.

Industrial plants, like power plants, steel mills, pulp or paper making plants, usually comprise means for conducting or storing fluids, e.g. pipe lines or fluid containers. It is a known issue that organic and inorganic matter deposits on the inner walls of these means for conducting or storing fluids, whereby an accumulation of fouling or scaling deposits at least partially blocks the flow through the conducting means and conducted or stored fluids may become contaminated. This is an unwanted occurrence that causes a number of operational problems such as plugging of equipment, inefficient usage of chemicals, increased utility costs, lost production due to downtime, corrosion, and downgraded products from increased dirt counts.

In principle, one can distinguish between fouling deposits on the one hand and scaling deposits on the other hand. Fouling deposits are organic deposits which often occur in the form of biofilms in aqueous systems. Such biofilms substantially consist of micro-organisms, e.g. bacteria, algae, fungi and protozoa. Contrary thereto, scale depositions occur from inorganic matter that have been identified include e.g. complexes of calcium (carbonate, oxalate, sulfate, silicates), aluminum (silicates, hydroxides, phosphates), barium sulfate, radioactive radium sulfate, and silicates of magnesium.

In order to avoid the accumulation of fouling deposits and in particular the growth of biofilms, biocides are added into the fluid concerned as countermeasures. Scaling deposits can be removed by adding chemical deposit control agents based on homopolymers, copolymers and terpolymers of acrylic acid, methacrylic acid, maleic acid and aspartic acid. Furthermore the chemical deposit control agents can be based on organic phosphonates and their derivatives, as well as on polyphosphates.

The dosage of these biocides and chemical deposit control agents has to be accomplished very carefully and conservative because they are very expensive and pose a health hazard. It is thus necessary to distinguish between scaling and fouling deposits and to determine the thickness of the scaling or fouling deposits.

A method and a device for high precision measurement of a characteristic of a fouling or scaling deposit inside a fluid vessel is disclosed in the prior art document WO 2009 /141 135 A1. An ultrasonic emission signal is emitted by an ultrasonic transducer towards a reflecting area inside the fluid vessel and a distance between the ultrasonic transducer and the reflecting area or between the ultrasonic transducer and a deposit onto the reflecting area is measured by means of evaluating the time-domain reflective signal of the reflecting area or of the deposit covering the reflecting area. The measured distance is compared to a reference distance which has been measured in an initial calibration measurement step without any deposits onto the reflecting area. The difference between the measured distance and the reference distance is a measure for the thickness of the deposition. A disadvantage of this method is that the real distance between the ultrasonic transducer and the reflective area changes e.g. with the temperature or the pressure inside the fluid vessel. Therefore, the current distance between the ultrasonic transducer and the reflective area at the time of measurement cannot accurately defined by a previously measured reference distance. Consequently, the measurement of the thickness of the deposits comprises an unknown offset depending on operational conditions, like pressure and temperature.

Industrial plants usually comprise multiple functional units, like boiler, heat exchanger, condenser, mixer, for instance. These multiple functional units are connected to each other, in particular in series and/or in parallel, via connection pipes and the like.

A problem of known devices for measuring fouling or scaling deposits in an industrial plant is that it is difficult to install suchlike measuring devices inside of the functional units because of e.g. limited installation space or excessively elevated temperatures inside the functional units. Consequently, the devices are provided usually at or in the connecting pipes between the functional units, even though the temperatures inside of the functional units are regularly higher than in the connecting pipes, in particular when the functional unit comprises e.g. a boiler. This is disadvantageous for the quality of the measurements because higher temperatures increase the growth of fouling, so that there is frequently a higher accumulation of deposits inside the functional units than inside of the connection pipes. Consequently, the results measured in the connecting tubes are falsified and the thickness of deposits in the relevant areas cannot be accurately determined.

SUMMARY

It is therefore an object of the present invention to provide a device and a method for detecting fouling and/or scaling deposits that allow a precise determination of deposits of fouling and/or scaling in a functional unit, even if the device cannot be installed directly inside of the functional unit because of e.g. limited installation space.

The object of the present invention is achieved by a device for detecting deposits in a reflecting area inside a liquid-bearing system comprising an ultrasonic transducer for emitting an ultrasonic emission signal towards the reflecting area and a detection means for detecting an ultrasonic reflection signal obtained by reflection of the ultrasonic emission signal in the area of the reflecting area, wherein the device further comprises heating means for increasing the temperature of the reflecting area.

According to the present invention, it is thereby advantageously possible to increase the temperature in the reflecting area, so that the actual conditions inside of a functional unit which is in fluid connection with the liquid-bearing system can actively be simulated at the installation area of the device. If the effective temperature in the area of the reflecting area is set by the heating means to the actual temperature inside of the functional unit, the accumulation of deposits in the reflecting area should be very similar to the accumulation of deposits in the functional unit. Advantageously, the accumulation of fouling and/or scaling deposits inside of the functional unit can be accurately measured without a need for installing the measuring unit directly into the functional unit. As a result of installing the device outside of the functional unit the device becomes better available for maintenance or repair work and installation costs can be reduced. A further advantage of this solution is that the device does not influence the functioning of the functional unit and that existing plants can easily be upgraded with suchlike measurement devices. The liquid-bearing system in the sense of the present inventions comprises preferably a pipe or a tube which is at least temporarily in fluid connection with a functional unit, preferably a supply line for supplying liquid to the functional unit or a drain line for draining liquid from the functional unit. It is also conceivable that the pipe or tube is connected parallel to the functional unit. Alternatively, the liquid-bearing system can also be a fluid container which is only temporarily in fluid connection with the functional unit. Preferably, the liquid-bearing system comprises a tube being a part of the device. Particularly preferably, the reflecting area is also a part of the device, wherein the reflecting area is located inside the tube and/or inside a tube wall. The tube is suitable for connection e.g. with a liquid-bearing pipeline of the functional unit. In particular, the device comprises a reflecting wall comprising and working as the reflecting area.

In particular, the wording "deposits" in the sense of the present inventions stands for any kind of organic or inorganic contaminants and deposits that occurs in liquid-bearing systems, like e.g. circuits, pipes or containers. Suchlike deposits occur e.g. in the form of films (also called "fouling"). These are formed primarily in aqueous systems at the interface with a solid phase. In case of micro-organisms caused films, they consist of a slimy layer in which micro-organisms (e.g. bacteria, algae, fungi, and protozoa) are embedded. As a rule, these films contain, other than the micro-organisms, primarily water and extra-cellular polymeric substances exuded by the micro-organisms which, in conjunction with the water, form hydro-gels and contain other nutrients or substances. Often, particles are included in the resulting slimy matrix that is found in the aqueous medium adjacent the interface. The films which occurs e.g. in papermaking plant are characterized by the fact that it contains a high proportion of fibers, fine substances, and inorganic pigments that are bound by the organic matrix. Such films typically are accompanied by protective exopolysaccharides ("slime", EPS) of microbiological sources and occur at the interface of these equipment surfaces and process water streams. Additionally, inorganic contaminants, such as calcium carbonate ("scale") and organic contaminants often deposit on such surfaces. These organic contaminants are typically known as "pitch" (e.g., resins from wood) and "stickies" (e.g., glues, adhesives, tape, and wax particles).

According to a preferred embodiment of the present invention, the heating means is directly coupled to the reflecting area, wherein preferably the heating means is rigidly coupled to the reflecting area by conducting means made of a thermally conductive material. It is herewith advantageously possible to achieve a efficient heat transfer from the heating means to the reflecting area. As a result, the energy consumption of the device can be reduced. This is particularly important when the reflecting area is heated permanently in order to continuously simulate the development of deposits similar to that in the functional units.

According to a particularly preferred embodiment of the present invention, the reflecting area is provided at least partially by a reflecting wall, preferably the reflecting wall comprises a wall portion of the liquid-bearing system and/or at least works as a wall portion of the liquid-bearing system. Advantageously, the reflecting wall is perfectly integrated into the wall of a liquid-bearing system without causing turbulences in the flow of the liquid through the liquid-bearing system when the liquid-bearing system comprises a liquid pipe. Preferably, the reflecting wall comprises an inner side facing the ultrasonic transducer and an outer side facing away from the ultrasonic transducer, wherein the heating means is connected to the outer side of the reflecting wall, so that a comparatively efficient heat transfer between the heating device and the reflecting wall is provided one the one hand and the flow of the liquid is not affected on the other hand.

Preferably, the device comprises a reflecting unit comprising the heating means, the heat conducting means and the reflecting wall, wherein the reflecting unit is preferably detachably connected to the liquid-bearing system in such a manner that the reflecting wall protrudes into an opening in the wall of the liquid-bearing system. It is herewith advantageously possible to assemble the device quickly and easily in the liquid-bearing system. In particular, the reflecting unit is connected to the liquid-bearing system by means of connecting joints, in particular a screw joint. In order to seal the opening in the liquid-bearing system, a sealing means is preferably provided between the reflecting wall and the wall of the liquid-bearing system surrounding the reflecting wall. The sealing means comprise e.g. a seal-ring in the form of an o-ring. The seal ring is located in groove in the wall of the liquid-bearing system or of the reflecting wall. In order to simplify the installation of the device, the device comprises preferably a measuring unit comprising the ultrasonic transducer and the detection means, wherein the measuring unit is detachably connected to the liquid-bearing system in such a manner that the measuring unit and the reflecting unit are located on opposite sides of the liquid-bearing system.

According to a preferred embodiment of the present invention, the heat conducting means comprises a holder having a recess, in which the heating means is accommodated, and wherein the heat conducting means comprises the reflecting wall, wherein an inner side of the reflecting wall faces the ultrasonic transducer. Preferably, the holder comprises a metal material having a comparatively good thermal conductivity. The holder is e.g. made of iron, steel, cooper, brass, stainless steel, silver, gold or the like. It is conceivable that the brass is Admiralty brass containing about 29% zinc, about 1% tin and about 70% copper. Preferably, the holder comprises or is made of copper, particularly preferably the holder comprises or is made of an alloy which comprises copper, nickel and iron (CuNiFe), or copper, nickel, iron and manganese (CuNiFeMn), or copper, nickel, iron and cobalt (CuNiFeCo). In a preferred embodiment, the holder is made of CuNiFeMn, wherein the weight percent of copper is in the range from 86 to 89,7, wherein the weight percent of nickel is in the range from 9 to 11, wherein the weight percent of iron is in the range from 1 to 2 and wherein the weight percent of manganese is in the range from 0,5 to 1. In a most preferred embodiment, the weight percent of nickel is 10 and the weight percent of iron is 1,6. In particular, the material of the holder corresponds to the material quoted in the official material data sheet "CuNi10Fe1Mn" issued 2012 from "Deutsches Kupferinstitut". The usage of the cited materials provides a holder with a very good thermal conductivity and simultaneously a good resistance to water.

Alternatively, the holder is made of a first material and comprises a coating of a second material in the reflecting area. Preferably, the first material comprises a good heat conductivity, like copper, wherein the second material preferably comprises a more corrosion resistant material and/or a material matching the material characteristics of the liquid-bearing system or of the functional unit to be emulated. Preferably, the coating is made of stainless steel. Preferably, the recess is provided in such a manner that the electrical cartridge heater is arranged parallel to the longitudinal axis of the tube, so that the efficiency of the heat transfer from the electrical cartridge heater to the reflecting wall through the holder can be increased.

According to a preferred embodiment, the reflecting unit comprises a heat insulator isolating the heating means and the reflecting wall from the wall of the fluid vessel surrounding the reflecting wall, preferably the heat insulator is provided between the reflecting wall and the connecting joints and particularly preferably the heat insulator encapsulates at least partially the heating means. Advantageously, the heat insulator prevents at least partially a heat transfer from the heating means to the wall of the fluid vessel surrounding the reflecting wall, so that the energy consumption for increasing the temperature of the reflecting wall can be reduced. The heat insulator is e.g. made of a polymer, like Polyether ether ketone (PEEK), for instance.

Preferably, the device comprises a temperature sensor, wherein the temperature sensor is preferably provided between the heating means and the reflecting area, so that the actual temperature in the reflecting area can be measured and monitored in order to avoid overheating and/or to setup a certain reference temperature. Preferably, the temperature sensor is integrated into the reflecting wall. It is conceivable that the outer side of the reflecting wall is provided with a cavity which at least partially encloses the temperature sensor. Preferably, the device comprises two temperature sensors which are located inside the holder and near the reflecting wall. The usage of two temperature sensors enables the determination of a temperature at the reflecting wall.

According to a preferred embodiment, the device comprises an analyzing unit which is configured to analyze the distribution of the temperature measured by the temperature sensor in order to determine whether deposits are located in the reflecting area and/or to determine the type and/or the thickness of a layer of deposits in the reflecting area. It is advantageously possible to determine whether deposits are located in the reflecting area simply by monitoring the distribution of the temperature in the reflecting area over time (by aid of the temperature sensor) because if the heating power remains constant and a layer of deposits growths on the reflecting area the effective thermal conductivity of the reflecting wall changes (decreases) which leads to corresponding signals in the distribution of the temperature over time detectable by the analyzing unit. The shape of the changes in the distribution is furthermore a measure for the type of the deposits, e.g. scaling or fouling deposits, because the heat transfer characteristic between the reflecting wall (e.g. made from metal) and fouling differs from the heat transfer characteristic between the reflecting wall (e.g. made from metal). In a similar way, also the thickness of the layer of deposits can be estimated by analyzing the shape of the changes in the distribution or by comparing the actual distribution with a reference distribution (which has been determined in reference measurements, for instance). Preferably, the thickness of the layer of scale deposits is determined by analyzing the run time of the ultrasonic reflection signal.

Another subject of the present invention is a method for detecting fouling and/or scaling deposits in a reflecting area inside a fluid vessel comprising a step of emitting an ultrasonic emission signal towards the reflecting area by an ultrasonic transducer and a step of detecting an ultrasonic reflection signal obtained by reflection of the ultrasonic emission signal in the area of the reflecting area by detection means, wherein the temperature of the reflecting area is increased by heating means.

It is herewith advantageously possible to actively control the temperature in the reflecting area. Consequently, the accumulation of deposits during arbitrarily and user-defined temperature conditions can be simulated. In particular, the method according to the present invention allows to indirectly determine the accumulation of deposits inside of a functional unit without installing the measurement device directly in this functional unit by simulating the actual temperature conditions inside the corresponding functional unit in the reflecting area.

Preferably, the reflecting area is heated by direct heat input from the heating means, wherein the heat is conducted from the heating means to the reflecting area via conducting means made of a thermally conductive material which is rigidly coupled to the reflecting area and to the heating means. It is herewith possible to establish a comparatively efficient heat transfer and to reduce energy consumption.

According to a preferred embodiment of the present invention, the temperature of the reflecting area is measured by a temperature sensor. Preferably, the heating means is controlled in dependency of a temperature determined by the temperature sensor, preferably the heating means is controlled in such a manner that the temperature determined by the temperature sensor corresponds to a predefined reference value. Advantageously, the temperature of the reflecting area is set to the desired predefined reference value and/or maintained on the reference temperature by means of a control loop. The reference value is preferably determined by measuring an actual temperature inside the corresponding functional unit which has to be monitored, so that the temperature in the reflecting area always corresponds with the actual temperature in the functional unit.

Further, the method comprises preferably a step of analyzing if fouling and/or scaling deposits are deposited in the reflecting area and to determine the thickness of the fouling and/or scaling deposits in the reflecting area. Particularly preferably, the method is capable to distinguish whether fouling or scaling deposits are deposited in the reflecting area.

According to a preferred embodiment of the present invention, the heating means is controlled in such a manner that the heating power provided by the heating means remains substantially constant. As described already above, it is advantageously possible to determine whether deposits are located in the reflecting area simply by monitoring the distribution of the temperature in the reflecting area over time (by aid of the temperature sensor) because if the heating power remains constant and a layer of deposits growths on the reflecting area the effective thermal conductivity of the reflecting wall changes which leads to corresponding detectable signals in the distribution of the temperature over time. Consequently, the distribution of the temperature measured by the temperature sensor is preferably analyzed by the analyzing unit in order to determine whether deposits are located in the reflecting area and/or in order to determine the thickness of a layer of deposits in the reflecting area and/or in order to determine if fouling and/or scaling deposits are deposited in the reflecting area. It is herewith advantageously possible to estimate if a layer of deposits are deposited inside of the functional units simply by monitoring the course of the temperature. If deposits are detected it is furthermore advantageously possible to estimate the type (e.g. scaling or fouling) and the quantity (e.g. thickness) of the accumulated deposits in the functional units simply by analyzing the shape of the changes in the course of the temperature over time. Consequently, appropriate countermeasures, like adding biocides into the liquid medium and into the liquid-bearing system, can be initiated, if necessary.

Preferably, the thickness of the layer of scale deposits is determined by analyzing the run time of the ultrasonic reflection signal.

It is conceivable that the measuring unit operates as disclosed in WO 2009/141 135 A1. For further embodiments and details of the method and the device according to the present invention, a reference is made to the disclosure of WO 2009/141 135 A1 which is incorporated herewith by reference.

According to a preferred embodiment of the present invention, the heating means is controlled in such a manner that the heating power provided by the heating means remains substantially constant, wherein the course of the temperature, measured by the at least one temperature sensor, over time is monitored and wherein an accumulation of deposits onto the reflecting wall is determined or notified when a change in the course of the temperature over time is detected. If the temperature of the reflecting wall remains constant, there is no measurable accumulation of deposits onto the reflecting wall 8, at all. But, if the temperature of the reflecting wall changes over time while the temperature and the flow rate of the liquid medium, as well as the heating power remain constant, this is an indicator that a layer of deposits has grown onto the reflecting wall because the layer of deposits changes the effective thermal conductivity of the holder and the reflecting wall. It is herewith advantageously possible to detect the accumulation of deposits onto the reflecting wall, independently of the kind of deposits. Based on the magnitude of temperature change over time, also a quantitative statement about the thickness of the biofilm can be made.

According to a preferred embodiment of the present invention, the a run time of the ultrasonic reflection signal is compared with a reference run time, if accumulation of deposits is determined or notified, wherein an accumulation of scale deposits is determined or notified, when both a change in the course of the temperature over time and a difference between the run time of the ultrasonic reflection signal and the reference run time are detected, and wherein an accumulation of fouling deposits is determined or notified, when a change in the course of the temperature over time and no significant difference between the run time of the ultrasonic reflection signal and the reference run time are detected. If the measured run time and the reference run time are substantially equal to each other, the ultrasonic emission signal has been reflected by the reflecting wall and not by a layer of deposits. Nevertheless, the determined temperature change in the reflecting wall is a measure for the presence of deposits on the reflecting wall. This means that the layer of deposits covering the reflecting wall is transparent for ultrasonic waves and therefore do not reflect the ultrasonic emission signal. Consequently, it can be determined that the layer of deposits mainly consists of fouling deposits (also referred to as organic deposits). If the measured run time is smaller than the reference run time, the ultrasonic emission signal has been reflected by the upper surface of the layer of deposits. In this case, it can be concluded that the layer of deposits is not transparent for ultrasonic waves. This means that the layer of deposits consists of scaling deposits comprising inorganic matter. The thickness of the layer of scale can directly be calculated from the difference between the measured run time and the reference run time by taking into account the speed of sound in water. It is herewith advantageously possible to detect the presence of any kind of deposits on the reflecting wall, to determine the type of deposits (organic or inorganic deposits) accumulated on the reflecting wall, and to calculate the thickness of the layer of deposits on the reflecting wall. Furthermore, the temperature conditions inside a functional unit can be simulated.

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference figures quoted below refer to the attached drawings.

DETAILED DESCRIPTION

Figure 1:
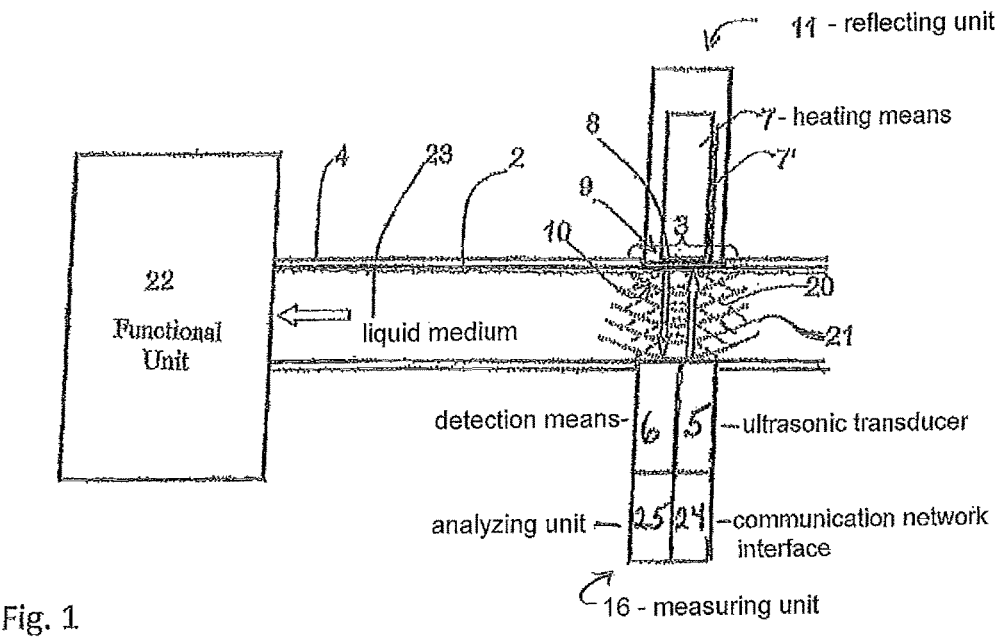
FIG. 1 illustrates schematically a device and a method for detecting and analyzing fouling and/or scaling deposits according to an exemplary first embodiment of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described of illustrated herein.

In FIG. 1, a device 1 for detecting fouling and/or scaling deposits 2 inside a liquid-bearing system 4 according to an exemplary first embodiment of the present invention is shown. In the present example, the liquid-bearing system 4 is a part of a paper making plant. The liquid-bearing system 4 comprises a hollow fluid pipe for conducting a liquid medium 23 into a functional unit 22 which is a heat exchanger or a boiler, for instance. The device 1 comprises a measuring unit 16 and a reflecting unit 11. The measuring unit 16 and the reflecting unit 11 are located on opposite sides of the liquid-bearing system 4 facing each other. The measuring unit 16 comprises an ultrasonic transducer 5 and a detection means 6. An ultrasonic emission signal 20 is emitted by the ultrasonic transducer 5 towards a reflecting area 3 and towards the reflecting unit 11 which comprises a reflecting wall 8 located inside the reflecting area 3. In order to detect and analyze fouling and/or scaling deposits 2 accumulated in the area of the reflecting area 10 onto the reflecting wall 8, a ultrasonic reflection signal 21 occurred through a reflection of the ultrasonic emission signal 20 in the reflecting area 10 is detected by the detection means 6 and analyzed by an analyzing unit 19. The reflecting wall 8 functions as a wall portion of the liquid-bearing system 4, so that an inner side 9 of the reflecting wall 8 facing the measuring unit 16 might be covered with scaling and/or fouling deposits 3 depending on the actual environmental conditions. If no deposits 2 are accumulated onto the reflecting wall 8, the inner side 9 of the reflecting wall 8 mainly serves as a reflecting surface for the ultrasonic signal. If scaling and/or fouling deposits 2 cover the reflecting wall 8, the ultrasonic signal is reflected at least partially at the surface of the deposits 2.

In order to simulate certain temperature conditions in the area of the reflecting area 3, the reflecting unit 11 comprises a heating means 7 for increasing the temperature in the reflecting area 3. In the present example, the heating means 7 comprises an electric cartridge heater. The cartridge heater is at least partially encapsulated by a heat conducting means 7' preferably made of a thermally conductive material, like metal. In particular, the conducting means 7' is rigidly coupled to both the cartridge heater and the inner side of the reflecting wall 8 in order to provide an efficient heat transport from the cartridge heater to the reflecting wall 8. The heater means 7 is connected via the conducting means 7' to an outer side 10 of the reflecting wall 8 facing away from the measuring unit 16. The heater means 7 is controlled in such a manner that the heating power of the heating means 7 remains substantially constant over time.

Furthermore, the reflecting unit 11 of the device 1 comprises a temperature sensor 15 provided between the reflecting area 3 and the heating means 7 in a cavity of the reflecting wall 8. The temperature sensor 15 continuously or discontinuously measures the temperature in the area of the reflecting wall 8. The device 1 optionally comprises an analyzing unit 25 for analyzing the distribution of the temperature over time in order to determine whether deposits 2 are located in the reflecting area 10. The analyzing unit 25 evaluates if a change in the distribution of the temperature occurs which does not depend only on temperature variations in the liquid. If suchlike changes in the distribution of the temperature occur, the presence of deposits 2 on the reflecting wall 8 can be determined. If the analyzing unit 25 detects the accumulation of deposits 2, the type and the thickness of the layer of deposits 2 is estimated on the basis of the shape of the changes in the distribution of the temperature.

As a result, it is possible to increase the temperature of the reflecting wall 8 by the heating means 7, so that the actual temperature conditions inside of the functional unit 22 can actively be simulated at the position of the reflecting wall 8. If the effective temperature in the area of the reflecting wall 8 is increased to the actual temperature inside of the functional unit 22 measured e.g. by an temperature sensor (not shown), inside of the functional unit 22 the accumulation of deposits 2 onto the reflecting wall 8 is very similar to the accumulation of deposits 2 inside of the functional unit 22. Consequently, the accumulation of fouling and/or scaling deposits 2 inside of the functional unit 22 can be measured accurately by the measuring unit 16, although the device 1 is not located inside of the functional unit 22.

If the presence of fouling or scaling deposits 2 is detected a corresponding control signal for initiating appropriate countermeasures, like adding biocides into the liquid medium 23 and into the liquid-bearing system 4, is generated. Preferably, the control signal depends on the type of deposits 2 (scaling or fouling) and the determined thickness of the layer of deposits 2. The control signal initiates e.g. a higher concentration of biocide in the liquid medium 23, if a thicker layer of fouling deposits 2 are determined, and a lower concentration of biocide, if the layer of fouling deposits 2 is thinner. It is conceivable that one or more pumps (not shown) are controlled directly by the control signal for pumping an appropriate amount of biocide into the liquid medium 23. Alternatively, one or more valves (not shown) are controlled by the control signal for leading a corresponding amount of biocide into the liquid medium 23. Preferably, the device 1 comprises a communication network interface 24 for transmitting the control signal and/or the measured data via a communications network, e.g. for recording, monitoring, controlling or maintenance purposes.

Figure 2A:
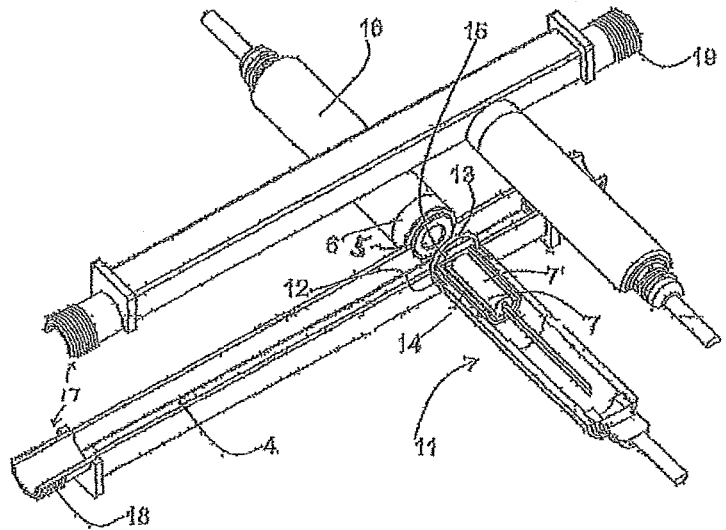
FIGS. 2a, 2b and 2c illustrate schematically a device for detecting fouling and/or scaling deposits according to an exemplary second embodiment of the present invention.
Figure 2B:
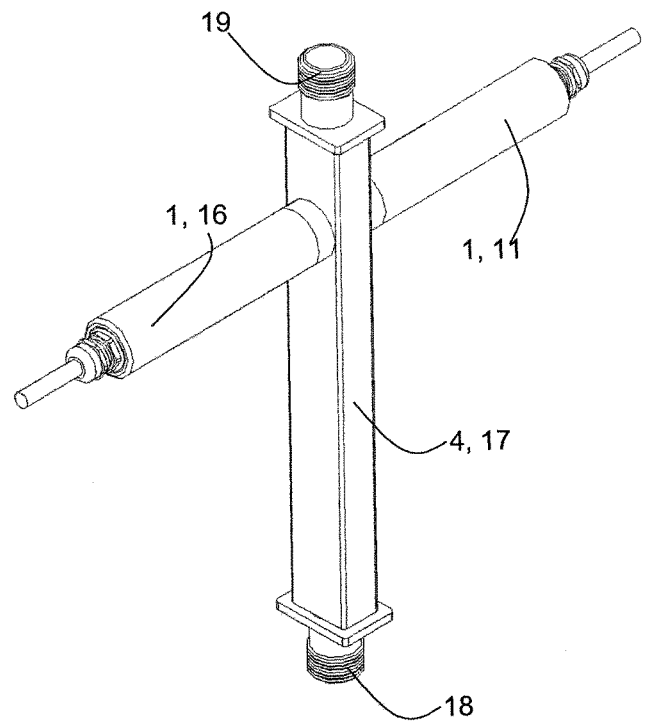
Figure 2C:
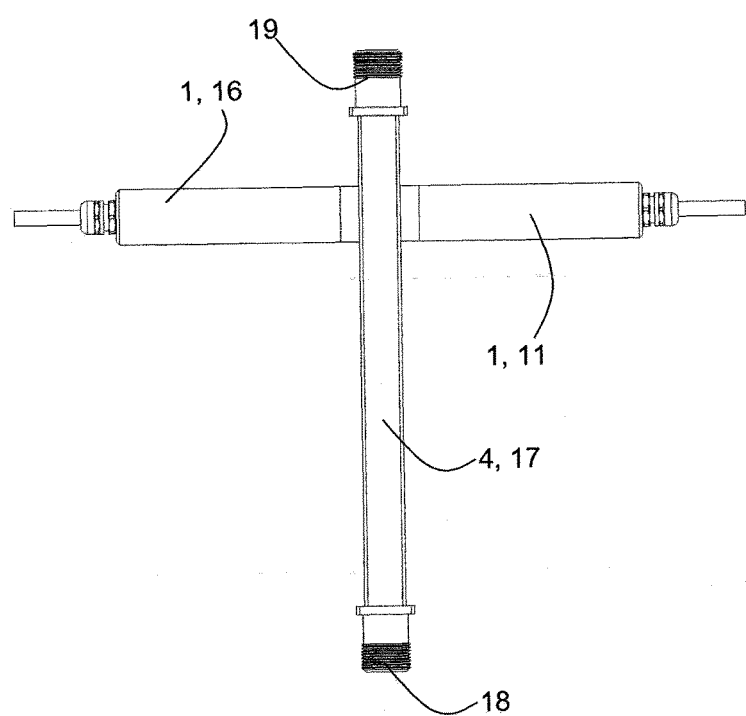

In FIGS. 2a, 2b and 2c, a device 1 for detecting fouling and/or scaling deposits 2 according to an exemplary second embodiment of the present invention is schematically shown. In principle, the second embodiment of the device 1 is similar to the first embodiment illustrated in FIG. 1, whereas the reflecting unit 11 of the device 1 according to the second embodiment is connected to the liquid-bearing system 4 by aid of connecting joints 12 and sealing means 13. The connecting joints 12 comprise a screw joint, so that the reflecting unit 11 can be mounted simply by inserting the reflecting wall 8 into the opening in the wall of the liquid-bearing system 4 and screwing to the wall of the liquid-bearing system 4. In order to seal the opening in the liquid-bearing system 4, the sealing means 13 is provided between the reflecting wall 8 and the wall of the liquid-bearing system 4 surrounding the reflecting wall 8. The sealing means 13 comprises a seal-ring in the form of an o-ring located in a groove in the wall of the liquid-bearing system 4. The reflecting unit 11 further comprises a heat insulator 14 at least partially encapsulating the heat conducting means 7' in order to avoid heat transfer from the heating means 7 to the walls of the liquid-bearing system 4 surrounding the reflecting wall. In particular the heat insulator 14 is partially provided between the heat conducting means 7' and the connecting joints 12 and between the reflecting wall 8 and the sealing means 13. The liquid-bearing system 4 is designed a tube 17 having an intake fitting 18 and an outflow fitting 19 for screw fitting the tube 17 into a pipeline of an industrial plant or to the functional unit 22. Alternatively, an electric panel heater (not shown) can be used as the heating unit 7, wherein the inner side 9 of the reflecting wall 8 is directly coupled to the heating panel of the electric panel heater.

Figure 3A:
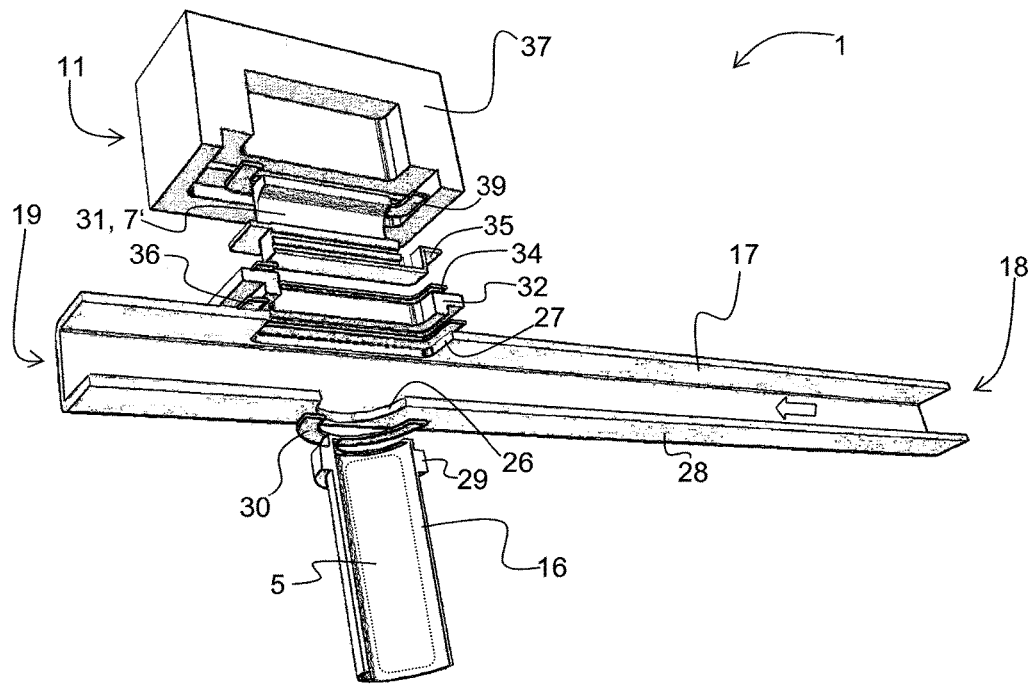
FIGS. 3a, 3b and 3c illustrate schematically a device for detecting fouling and/or scaling deposits according to an exemplary third embodiment of the present invention.
Figure 3B:
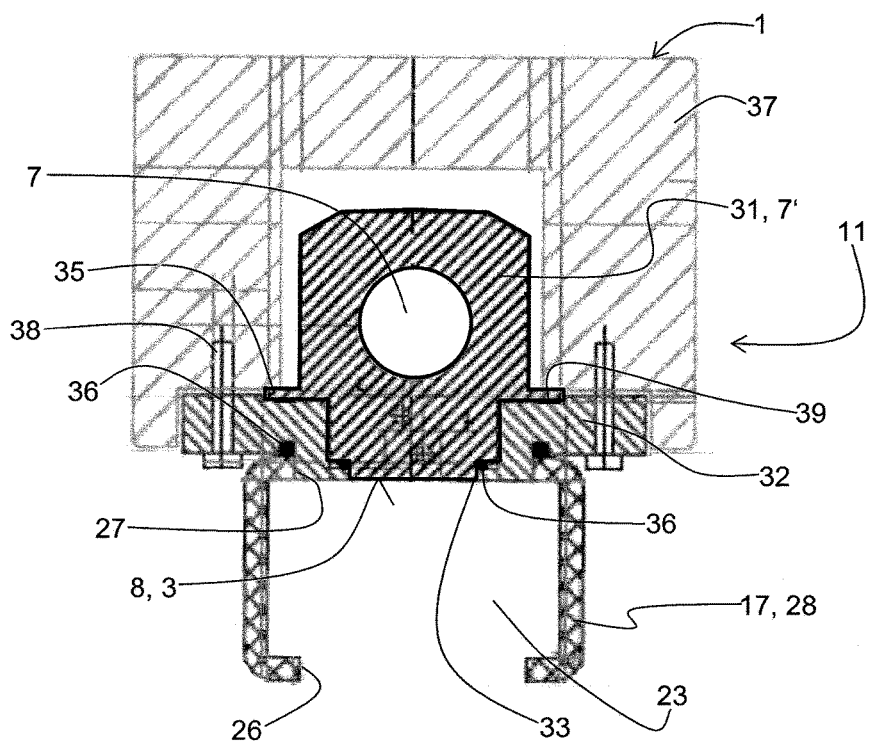
Figure 3C:
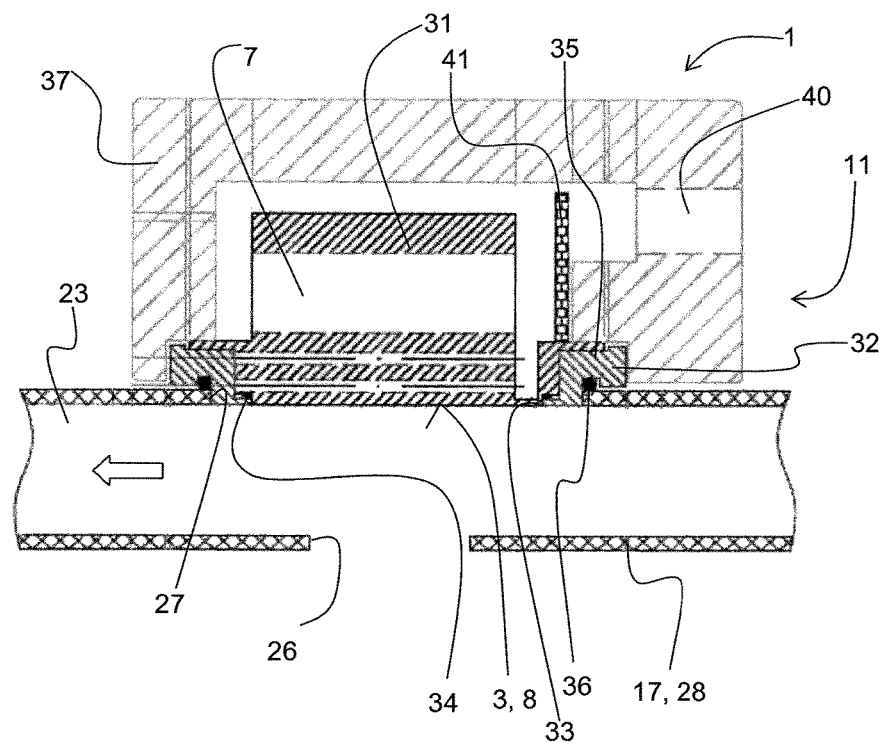

In FIGS. 3a, 3b and 3c, a device 1 for detecting fouling and/or scaling deposits 2 according to an exemplary third embodiment of the present invention is schematically shown. The device 1 comprises a tube 17 with an intake fitting 18 and an outflow fitting 19. The tube 17 is integrated into a liquid-bearing system 4 of e.g. a paper making plant (not shown). The liquid-bearing system 4 comprises hollow fluid pipes for conducting a liquid medium 23 into a functional unit 22 which is a heat exchanger or a boiler of the paper making plant, for instance. The liquid medium 23 flows at least partially also through the tube 17.

FIG. 3a shows a cross section of an exploded view of the device 1, whereas FIG. 3b shows a cross section of the device 1 perpendicular to the longitudinal direction of the tube 17 and FIG. 3c shows a cross section of the device 1 parallel to the longitudinal direction of the tube 17.

In the present example, the tube 17 is provided with a rectangular cross section. The tube wall 28 comprises a first opening 26 and a second opening 27 which are provided on opposite sides of the tube 17. The device 1 comprises a measuring unit 16 which is located partially inside the first opening 26. The measuring unit 16 has a flange 29 which is sealed to the outer surface of the tube wall 28 by a first seal ring 30. Furthermore, the device 1 comprises a reflecting unit 11 located partially inside the second opening 27. The measuring unit 16 and the reflecting unit 11 are located on opposite sides of the tube 17. The reflecting unit 11 comprises a reflecting area 3 facing the measuring unit 16.

In principle, the measuring unit 16 has the same design as the measuring unit 16 described on the basis of FIGS. 1 and 2a to 2c. The measuring unit 16 comprises an ultrasonic transducer 5 and a detection means 6. An ultrasonic emission signal 20 is emitted by the ultrasonic transducer 5 towards a reflecting area 3 and towards the reflecting unit 11 which comprises a reflecting wall 8 located inside the reflecting area 3. The reflecting wall 8 is also located inside the second opening 27. In order to detect and analyze fouling and/or scaling deposits 2 accumulated onto the reflecting wall 8, a ultrasonic reflection signal 21 occurred through a reflection of the ultrasonic emission signal 20 in the reflecting area 10 is detected by the detection means 6 and analyzed by an analyzing unit 19. The reflecting wall 8 functions as a wall portion of the liquid-bearing system 4, so that an inner side 9 of the reflecting wall 8 facing the measuring unit 16 might be covered with scaling and/or fouling deposits 3 depending on the actual environmental conditions in the liquid-bearing system 4.

The design of the reflecting unit 11 differs from the design shown in FIGS. 1 and 2a to 2c. The reflecting unit 11 comprises a heating means 7 for increasing the temperature in the reflecting area 3, so that certain temperature conditions, in particular the temperature conditions inside of the functional unit 22, can be simulated in the area of the reflecting area 3. The heating means 7 comprises a cylindrical electric cartridge heater which is arranged parallel to the main axis of the tube 17 in order to achieve a more efficient heat input from the heated surface of the electric cartridge heater into the reflecting area. The cylindrical electric cartridge heater is integrated into a recess of a holder 31 fixing the cartridge heater and acting as a heat conducting means 7'. The holder 31 works as a heat conducting means 7'. Particularly, the holder 31 is made of metal with a comparatively good thermal conductivity, e.g. iron, stainless steel, copper and/or brass. In the present example, the holder 31 is made of an alloy of copper, nickel, iron (CuNiFe), preferably copper, nickel, iron and manganese (CuNi10Fe1, 6Mn). The CuNiFeMn material ensures a comparatively high resistance to water and simultaneously a good thermal conductivity. One side of the holder 31 comprises the reflecting wall 8 located inside the second opening 27, so that the heat generated by the electric cartridge heater is transported by thermal conduction within the holder 31 directly to the reflecting wall 8.

A flange 35 of the holder 31 is supported by a carrier 32. The carrier 32, which is preferably made from synthetic or ceramic materials, works as the heat insulator 14 to reduce the heat transfer from the holder 31 to the tube wall 28. The carrier 32 is provided also in the second opening 27 and comprises a third opening 33, in which the reflecting wall 8 is located. The flange 35 of the holder 31 is sealed against an inner surface of the carrier 32 by a second seal ring 34. The carrier 32 is sealed against the outer surface of the tube 17 by a third seal ring 36. The carrier 32 is connected to a housing 37 by screws 38. The carrier 32 and the housing 37 completely encapsulate the holder 31 together with the cartridge heater, except of the reflecting wall 8. The flange 35 of the holder 31 is sealed against the housing 37 by a fourth seal ring 39. Furthermore, the flange 35 of the holder 31 is clamped between the housing 37 and the carrier 32 which are pressed together by the screws 38. The second seal ring 34, the third seal ring 36 and the fourth seal ring 39 ensures that no water enters the housing 37 and comes into contact with the cartridge heater. The housing 31 comprises a service opening 40 through which power supply and control cables are running. Inside the housing 37, an additional sealing means 41 is provided, e.g. a water barrier. The whole device 1 is comparatively compact. It is conceivable that the measuring unit 16 and the reflecting unit 11 are pressed against the tube 17 by fixing means (not shown), like screws or the like, which extend beside and past the tube 17 from the measuring unit 16 to the reflecting unit 11.

The device 1 comprises two temperature sensors (not shown) provided near the reflecting wall 8 in order to accurately determine the temperature of the reflecting wall 8. It is conceivable that the device 1 comprises a sensor measuring the temperature of the liquid medium 23 passing the reflecting wall 8. Furthermore, the device 1 can be provided with a flow meter measuring the flow rate of the liquid medium 23 through the tube 17. The device 1 comprises an analyzing unit 24 for analyzing at least the temperature data of the temperature sensors and the measuring data of the measuring unit 16 to determine, if a layer of deposits 2 is deposited onto the reflecting wall 8, and, if the presence of deposits 2 are detected, to distinguish, whether fouling or scaling deposits 2 are accumulated onto the reflecting wall 8.

The following explains how the detection of deposits 2 and the distinction between different kinds of deposits 2 with the device 1 according to the third embodiment works; The liquid medium 23 is passed through the tube 17. The electric cartridge heater is switched on and controlled in such a manner that the temperature of the reflecting wall 8 is set to a desired temperature. The desired temperature corresponds to the actual working temperature of a heat transfer surface inside the functional unit 22, for instance. Afterwards, the heating power is kept constant and the course of the temperature of the reflecting wall 8 over time is monitored. If the temperature remains constant, there is no measurable accumulation of deposits 2 onto the reflecting wall 8, at all. But, if the temperature of the reflecting wall 8 changes over time while the temperature and the flow rate of the liquid medium 23 remain constant, this is an indicator that a layer of deposits 2 has grown onto the reflecting wall 8 because the layer of deposits 2 changes the effective thermal conductivity of the holder 31. In other words, the measuring unit 16 notifies the presence of deposits 2 on the heated reflecting wall 8 by detecting a temperature change of the reflecting wall 8 over time.

When the presence of deposits 2 are detected, the measuring unit 16 will be started to determine the thickness of the layer of deposits 2 by analyzing the run time of an ultrasonic reflection signal 21. The measuring unit 16 comprises an ultrasonic transducer 5 emitting an ultrasonic emission signal 20 across the tube 17 towards the reflecting wall 8. The ultrasonic emission signal 20 is reflected in the reflecting area 3 back to the ultrasonic transducer 5 either by the reflecting wall 8 or by the layer of deposits 2 covering the reflecting wall 3. The reflected signal is referred to as ultrasonic reflection signal 21 measured by detection means 6. The run time of the ultrasonic reflection signal 21 is determined and compared to a reference run time. The reference run time corresponds to the run time of an ultrasonic reflection signal without accumulation of deposits 2 in the reflecting area 3 under the same conditions. For example, the reference run time has been initially measured by the measuring unit 16 immediately after the device 1 has been integrated into the liquid bearing system 4 and after the holder 31 has been heated to the desired temperature. At this time, growth of deposits 2 has not yet been taken place on the reflecting wall 8.

If the measured run time and the reference run time are substantially equal to each other, the ultrasonic emission signal 20 has been reflected by the reflecting wall 8 and not by a layer of deposits 2. Nevertheless, the determined temperature change in the reflecting wall 8 is a measure for the presence of deposits 2 on the reflecting wall 8. This means that the layer of deposits 2 covering the reflecting wall 8 is transparent for ultrasonic waves and therefore do not reflect the ultrasonic emission signal 20. Consequently, it can be determined that the layer of deposits 2 mainly consists of fouling deposits (also referred to as organic deposits). In particular, the layer of deposits 2 must be a biofilm. Based on the magnitude of temperature change over time, a quantitative statement about the thickness of the biofilm can be made.

If the measured run time is smaller than the reference run time, the ultrasonic emission signal 20 has been reflected by the upper surface of the layer of deposits 2. It can be concluded that the layer of deposits 2 is not transparent for ultrasonic waves. This means that the layer of deposits 2 consists of scaling deposits comprising inorganic matter. The thickness of the layer of scale can directly be calculated from the difference between the measured run time and the reference run time by taking into account the speed of sound in water.

In summary, the described device 1 and method enables to detect the presence of any deposits 2 on the reflecting wall 8, to determine the type of deposits 2 (organic or inorganic deposits) accumulated on the reflecting wall 8, and to calculate the thickness of the layer of deposits 2 on the reflecting wall 8. Furthermore, the temperature conditions inside a functional unit 22 can be simulated.

If the presence of deposits 2 is detected and the type and thickness of the layer of deposits 2 are determined, a corresponding control signal for initiating appropriate countermeasures, like adding biocides into the liquid medium 23 and into the liquid-bearing system 4, is generated. Preferably, the control signal depends on the type of deposits 2 (scaling or fouling) and the determined thickness of the layer of deposits 2. The control signal initiates e.g. a higher concentration of biocide in the liquid medium 23, if a thicker layer of fouling deposits 2 are determined, and a lower concentration of biocide, if the layer of fouling deposits 2 is thinner. It is conceivable that one or more pumps (not shown) are controlled directly by the control signal for pumping an appropriate amount of biocide into the liquid medium 23 and in particular towards the functional unit 22. Alternatively, one or more valves (not shown) are controlled by the control signal for leading a corresponding amount of biocide into the liquid medium 23. Preferably, the device 1 comprises a communication network interface 24 for transmitting the control signal and/or the measured data via a communications network, e.g. for recording, monitoring, controlling or maintenance purposes.

Figure 4:
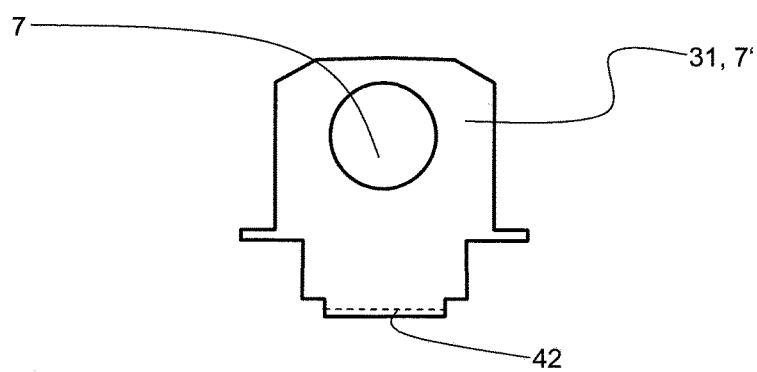
FIG. 4 illustrates schematically a holder of a device for detecting fouling and/or scaling deposits according to an exemplary fourth embodiment of the present invention.

In FIG. 4, the schematic detail view of a holder 31 of a device 1 according to an exemplary fourth embodiment of the present invention is shown. In principle, the fourth embodiment corresponds to the third embodiment, wherein the holder 31 is made of a high conductivity metal, like copper, wherein the reflecting wall 3 of the holder 31 comprises a coating 42 comprising a more corrosion resistant material, like stainless steel. It is also conceivable that the coating 42 is made of a material which matches the actual metallurgy of the liquid-bearing system and/or the heat exchanger to be emulated, e.g. stainless steel.

REFERENCE SIGNS 1 device
2 deposits
3 reflecting area
4 liquid-bearing system
5 ultrasonic transducer
6 detection means
7 heating means
7' heat conducting means
8 reflecting wall,
9 inner side
10 outer side
11 reflecting unit
12 connecting joints
13 sealing means
14 heat insulator
15 temperature sensor
16 measuring unit
17 tube
18 intake fitting
19 outflow fitting
20 ultrasonic emission signal
21 ultrasonic reflecting signal
22 functional unit
23 liquid medium
24 communication network interface
25 analyzing unit
26 first opening
27 second opening
28 tube wall
29 flange of measuring unit
30 first seal ring
31 holder
32 carrier
33 third opening
34 second seal ring
35 flange of holder
36 third seal ring
37 housing
38 screw
39 fourth seal ring
40 service opening
41 sealing means
42 coating

We claim:

1. A device for detecting deposits in a heated reflecting area inside a liquid-bearing system comprising a measuring unit, a reflection unit and an analyzing unit, wherein the measuring unit comprises an ultrasonic transducer for emitting an ultrasonic emission signal towards the heated reflecting area of the reflection unit, and a detection means for receiving the ultrasonic emission signal that is reflected back from the heated reflecting area of the reflection unit or the reflection of the ultrasonic emission signal from a deposit in the heated reflecting area, and analyzed by the analyzing unit, wherein the reflecting unit further comprises a heating means and temperature sensors for increasing the temperature of the reflecting area, wherein the heating means is rigidly coupled to the reflecting area by heat conducting means made of a thermally conductive material, the heat conducting means comprising a holder having a recess in which the heating means is accommodated and wherein the heat conducting means comprises the reflecting wall where an inner side of the reflecting wall faces the ultrasonic transducer.

2. The device according to claim 1, wherein the device comprises a reflecting unit comprising the heating means, the heat conducting means and the reflecting wall, wherein the reflecting unit is detachably connected to the liquid-bearing system in such a manner that the reflecting wall protrudes into an opening in the wall of the liquid-bearing system.

3. The device according to claim 2, wherein the reflecting unit is connected to the liquid-bearing system by means of connecting joints, wherein sealing means are provided between the reflecting wall and the wall of the liquid-bearing system surrounding the reflecting wall.

4. The device according to claim 3, wherein the reflecting unit comprises a heat insulator isolating the heating means and the reflecting wall from the wall of the liquid-bearing system surrounding the reflecting wall wherein the heat insulator is provided between the reflecting wall and the connecting joints and/or the heat insulator encapsulates at least partially the heating means.

5. The device according to claim 4, wherein the holder is selected from the group consisting of copper an alloy of copper, nickel and iron and an alloy of copper, nickel, iron and manganese.

6. The device according to claim 5, wherein the holder comprises a stainless steel coating.

7. The device according to claim 6, wherein the device comprises at least one temperature sensor, wherein the at least one temperature sensor is provided near or integrated into the reflecting wall.

8. The device according to claim 7, wherein the device comprises a measuring unit comprising the ultrasonic transducer and the detection means, wherein the measuring unit is detachably connected to the liquid bearing system in such a manner that the measuring unit and the reflecting unit are located on opposite sides of the liquid-bearing system.

9. The device according to claim 8, wherein the device comprises an analyzing unit which is configured to analyze the distribution of the temperature measured by the at least one temperature sensor in order to determine whether deposits are located in the reflecting area and/or to determine the type and/or the thickness of a layer of deposits in the reflecting area.

10. The device according to claim 3, wherein the connecting joint is a screw joint.

11. A method for detecting fouling and/or scaling deposits in a heated reflecting area of a liquid-bearing system, comprising emitting and receiving from a measuring unit an ultrasonic signal generated by an ultrasonic transducer, wherein the ultrasonic signal is emitted towards a reflecting unit having a heating means for heating the reflecting area and wherein the emitted signal is reflected back to the measuring unit and a detection means therein; and a step of detecting the reflected ultrasonic signal by the detection means; and analyzing the distribution of the temperature over time by an analyzing unit, wherein the temperature of the heated reflecting area is measured by at least one temperature sensor and wherein the temperature of the reflecting area is controlled by the heating means which is rigidly coupled to the reflecting area via a thermally conductive material, and wherein the temperature of the heating means is controlled in such a manner that the temperature determined by the temperature sensor corresponds to a reference value.

12. The method according to claim 11, wherein a distribution of the temperature measured by the temperature sensor is analyzed by an analyzing unit in order to determine whether deposits are located in the reflecting area and/or to determine the type and/or the thickness of a layer of deposits in the reflecting area.

13. The method according to claim 12, wherein the heating means is controlled in such a manner that the heating power provided by the heating means remains substantially constant, wherein the course of the temperature, measured by the at least one temperature sensor, over time is monitored and wherein an accumulation of deposits onto the reflecting wall is determined when a change in the course of the temperature over time is detected.

14. The method according to claim 13, wherein a run time of the ultrasonic reflection signal is compared with a reference run time, if accumulation of deposits is determined, wherein an accumulation of scale deposits is determined, when both a change in the course of the temperature over time and a difference between the run time of the ultrasonic reflection signal and the reference run time are detected, and wherein an accumulation of fouling deposits is determined, when a change in the course of the temperature over time and no significant difference between the run time of the ultrasonic reflection signal and the reference run time are detected.

* * * * *